United States Patent [19]

Nelson et al.

[11] Patent Number: 4,707,443
[45] Date of Patent: Nov. 17, 1987

[54] SOLUBLE INTERLEUKIN-2 RECEPTOR AS A DISEASE INDICATOR AND A METHOD OF ASSAYING THE SAME

[75] Inventors: David Nelson; William Biddison; Laurence Rubin, all of Bethesda; Warner Greene, Potomac, all of Md.; Warren Leonard, Washington, D.C.; Robert Yarchoan, Bethesda, Md.

[73] Assignee: The United States of America as represented by the Secretary of the Department of Health and Human Services, Washington, D.C.

[21] Appl. No.: 724,897

[22] Filed: Apr. 19, 1985

[51] Int. Cl.$^4$ ............ G01N 33/53; G01N 33/577; C12N 15/00
[52] U.S. Cl. .................... 435/7; 435/68; 435/172.2; 435/240.27; 435/810; 436/501; 436/531; 436/547; 436/548; 436/800; 436/808; 436/809; 436/83; 530/387; 935/89; 935/95; 935/106; 935/110
[58] Field of Search ........... 436/501, 547, 548, 531, 436/800, 804, 808, 809, 813; 435/7, 68, 172.2, 240, 810, 948; 260/112 R; 935/89, 95, 106, 110; 530/387

[56] References Cited

U.S. PATENT DOCUMENTS

| | | | |
|---|---|---|---|
| 4,376,110 | 8/1983 | David et al. | 436/513 |
| 4,411,993 | 10/1983 | Gillis | 435/68 |
| 4,536,479 | 8/1985 | Vander-Mallie | 436/537 |
| 4,545,985 | 8/1985 | Pastan et al. | 424/85 |
| 4,578,335 | 3/1986 | Urdal et al. | 435/68 |

FOREIGN PATENT DOCUMENTS

| | | | |
|---|---|---|---|
| 0102601 | 3/1984 | European Pat. Off. | 436/548 |
| 0111344 | 6/1984 | European Pat. Off. | 436/548 |

OTHER PUBLICATIONS

Kohler et al, Nature, vol. 256, pp. 495-497, 1975.
Depper et al, Journal of Immunology, vol. 131(2), pp. 690-696, 1983.

Primary Examiner—Christine M. Nucker
Attorney, Agent, or Firm—Holman & Stern

[57] ABSTRACT

The present invention discloses a sandwich method and a kit for assaying interleukin-2 receptor (IL-2R) in a sample. The method comprises determining reactivity of said sample with a plurality of ligands, each said ligand having binding affinity for a specific site on the receptor, said site being different for each said ligand and distinct from interleukin-2 binding site on the receptor. The invention also discloses a method of detecting such disturbed or abnormal conditions in humans which release soluble IL-2R in the body fluid.

18 Claims, 7 Drawing Figures

SOLUBLE INTERLEUKIN-2 RECEPTOR (HUT 102/B2)

$M_r \times 10^{-3}$

SOLUBLE INTERLEUKIN-2 RECEPTOR AS A DISEASE INDICATOR AND A METHOD OF ASSAYING THE SAME

BACKGROUND OF THE INVENTION

1. Technical Field

The present invention is related to soluble interleukin-2 receptor (IL-2R) and a method of assaying the same. More particularly, the present invention is related to the discovery of soluble, IL-2R in human body fluid as a result of disturbed body function and a solid phase immunoassay for quantitative determination thereof.

2. State of the Art

The ligand interleukin-2 (IL-2) and its receptor (IL-2R) per se, are well known entities. Interleukin-2 or T-cell growth factor as it is sometimes called, is a lymphokine, synthesized and secreted by lectin—or antigen-activated T-cells. The reported biological activities of IL-2 include stimulation of long-term in vitro growth of activated T-cell clones, induction of cytotoxic T-cell reactivity and the like. It is believed that IL-2 exerts its biological effects by interacting with specific high affinity receptors (IL-2R) on the surface of activated T-cells.

In contrast to hormone mediated systems, cellular activation is a prerequisite for the induction of both the ligand (IL-2) and its receptor (IL-2R), the latter being expressed rapidly at the cell surface in a time-dependent and heterogeneous manner (Cantrell, et al, Science, 224: 1312–1316, 1984).

When certain human cells are stimulated or otherwise activated, they manufacture and express newly synthesized molecules on their cell surfaces and also release these molecules in a soluble form. Hence, the detection of these molecules, which are not expressed by resting or unactivated cells, can serve as an indicator or "footprint" of cellular activation. As will be described more fully herein infra, it has been discovered that IL-2R is produced in the soluble form and circulated in the body fluid as a result of immune-activation or under certain malignant conditions, particularly in lymphoreticular malignancies.

Heretofore, the measurement of IL-2 receptors (IL-2R) was limited to the assessment of cell-associated IL-2R by a variety of immunological techniques, involving several monoclonal antibodies against the human IL-2R. The observation of a soluble or released form of this molecule has heretofore not been reported. Therefore, this soluble molecule has never been measured in a body fluid. Hence, the detection of a soluble IL-2R molecule in humans under certain conditions is a new discovery.

With regard to cell-associated IL-2R, the quantitative measurement of IL-2R has been accomplished by binding of the monoclonal antibody followed by cellular analysis with a fluorescence-activated cell sorter (FACS) or similar machine (costing approximately $80,000–200,000). Such an analysis provides information about the number of cells expressing receptor and the amount of antibody bound, but does not provide a quantitative estimate of the number of receptors. The latter can be accomplished with an assay using radiolabeled monoclonal of known specific activity. However, such tests are tedious and require radionuclides which pose problems of safety and disposal.

In contrast, the Enzyme-Linked-Immunosorbent Assay (ELISA) of the present invention for IL-2R described in detail herein is quantitative, rapid, sensitive, inexpensive, and employs enzyme rather than radioactivity to detect IL-2R. The necessary reagents could be packed in a rather small box or kit and would have a "shelf-life" of about one year. The instrument necessary to "read" the assay can be a simple spectrophotometer which is available in virtually every clinical hospital laboratory. In addition to the method described herein, this solid-phase immunoassay has also been performed with alkaline phosphatase conjugated monoclonal antibody (7G7/B6) directly, instead of the FITC-conjugated 7G7/B6 and alkaline phosphatase conjugated rabbit anti-FITC.

SUMMARY OF THE INVENTION

It is, therefore, an object of the present invention to provide a quantitative, rapid, sensitive and inexpensive method of determining IL-2R.

It is a further object of the present invention to provide a solid phase immunoassay for quantitative determination of IL-2R.

It is a still further object of the present invention to provide a monoclonal antibody having specific binding affinity for an epitope of IL-2R, said epitope being different from IL-2 binding site and from a heteroantibody binding site of the receptor.

It is yet another object of the present invention to provide a "sandwich" Enzyme-Linked-Immunosorbent Assay (ELISA) for IL-2R.

An additional object of the present invention is to provide a method for monitoring, detecting or screening such malignant, therapeutic, autoimmune, or pathophysiological states in humans of which soluble IL-2R level in the body fluid reflects an indicative index.

A still further object of the present invention is to provide a kit containing various components of the present sandwich ELISA for detecting soluble IL-2R, particularly in human plasma or serum.

Other objects and advantages will become apparent as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

These and other objects of the present invention are achieved by an inexpensive, rapid, sensitive and quantitative assay for detecting the presence of soluble IL-2 receptor in a sample, comprising a monoclonal antibody having specific binding affinity for an epitope of the receptor, said epitope being different from IL-2 binding site and from a heteroantibody binding site of the receptor.

Although any materials and methods similar or equivalent to the materials and methods described hereunder can be used in the testing or practice of the present invention, the preferred materials and methods are now described. All publications mentioned hereunder are incorporatad herein by reference.

MATERIALS AND METHODS

Source of Normal Cells and Cell Lines:

Peripheral blood mononuclear cells (PBMC) were prepared from normal heparinized venous blood following standard procedure well known in the art. IL-2 dependent cell lines were made and maintained as described infra. The HTLV positive T-cell line HUT 102B2 has been well characterized (Poeisz, et al, Nature 294, 268-271, 1981) and was provided by Dr. N. Goldman, NIH, Bethesda, MD. The T-cell lines MOLT-4, CEM, and JURKAT (Uchiyama, et al, J. Immunol. 126, 1393-1397, 1981 and Robb, et al, J. Exp. Med. 160, 1126-1146, 1984), as well as the human Epstein-Barr virus (EBV) transformed B-lymphoblastoid lines were provided by Dr. R. Quinones, NIH, Bethesda, MD. The pre B-cell lines NALM-1 and NALL-1 (Korsmeyer, et al, J. Clin. Invest. 71, 301-313, 1983), and the B-cell lines NU-DHL1 and SU-DHL6 (Winter, et al, Blood 63, 140-146, 1984) were obtained from Dr. S. Korsemeyer of NIH, Bethesda, MD. A second monoclonal antibody against the IL-2R, termed anti-Tac as described by Uchiyama, et al, supra, was obtained from Dr. T. Waldmann, NIH, Bethesda, MD.

Culture Stimulants:

Phytohaemagglutinin (PHA/GIBCO) was used at a final dilution of 1/200 (v/v), purified OKT-3 at 10 ng/ml, Tetanus toxoid (Massachusetts Dept. of Public Health) at a final concentration of 6Lf Units/ml, and Pokeweed mitogen (PWM/Gibco) at a final dilution of 1/100 (v/v).

Cells and Cell Cultures:

PHA activated lymphoblasts from normal individuals were produced in bulk culture by adding 10 ml of peripheral blood mononuclear cells (PBMC) at $1 \times 10^6$ cells/ml suspended in 1640 media containing 5% heat-inactivated (56° C., 30 minutes) fetal calf serum (FCS) (Gibco) to tissue flasks (Costar #3275, Cambridge, MA) with PHA (Gibco) at a final dilution of 1/200 (v/v), and incubated for 72 hrs in a humidified 5% CO in air atmosphere at 37° C. Concanavalin A (Con A) (Sigma Chemicals, St. Louis, MO) stimulated PBMC were prepared identically with 10 μg/ml of Con A. B cell lymphoblastoid lines were from normal PBMC transformed with the B95-8 strain of Epstein-Barr virus.

The HTLV-1 positive T-cell leukemia line, HUT 102B2 was maintained in vitro by serial passage in antibiotic suplemented RPMI 1640 containing 10% FCS and added Gentamycin (50 μg/ml, Schering Corp. Kennelworth, NJ). An IL-2 dependent T-cell line was prepared from 72 hr PHA lymphoblasts by resuspending the cells at $1 \times 10^6$ cells/ml in antibiotic supplemented 1640 media with 5% FCS and 10% (v/v) lectin-free IL-2 (cellular Products, Buffalo, NY) and reculturing for two passages of 3-5 days each. The responsiveness of such cells to IL-2 and the inhibition of IL-2 induced proliferation by 7G7/B6 or anti-Tac was tested by incubating $50 \times 10^3$ cells in 200 μl of media in quadruplicate in the wells of 96 well microtitre plates (Costar #3596) for 72 hrs without added IL-2, or with added IL-2 and equivalent concentrations of either 7G7/B6 or anti-Tac. Cultures were pulsed with 1 μCi of $^3$H-Thymidine (New England Nuclear, Boston, MA, 20 Ci/mmol) for the final 4 hrs of culture. The assessment of the proliferative and cytotoxic responses of mixed leucocyte cultures (MLC) in the presence or absence of 7G7/B6 were performed as described by Uchiyama, et a, J. Immunol. 126: 1398, 1981. In addition, untreated allostimulated cells were coated with 7G7/B6 or anti-Tac and separated into positive and negative populations employing Sephadex G-200 anti-mouse Fab columns as described by Uchiyama, et al, supra. These separated cells were then tested for cytotoxic effector activity as described by Uchiyama, et al, supra. T-cells and non T-cells were separated by AET treated sheep erythrocyte rosetting as described by Tosato, et al. NEJM 301:1133, 1979.

Stimulated Cultures:

Cultures stimulated with PHA or OKT-3 contained $5 \times 10^5$ cells in 2 mls of RPMI 1640 with 10% heat inactivated fetal calf serum (FCS) supplemented with Penicillin 100 U/ml and Streptomycin 100 μg/ml. Cultures stimulated with PWM contained $2 \times 10^6$ cells in 2 mls of the same medium. Cultures stimulated with Tetanus toxoid or allogeneic cells contained $3 \times 10^6$ and $2 \times 10^6$ cells/culture, respectively, in 2 mls of the same media containing 10% pooled human plasma. Allogeneic cultures consisted of $1 \times 10^6$ responder PBMC and $1 \times 10^6$ irradiated (3000 R) stimulator PBMC. Triplicate replicate cultures were established in 24-well plates (Costar, Cambridge, MA) and incubated at 37° C. in a humidified 5% $CO_2$ and air atmosphere. The cultures were harvested at various times, the replicates pooled and centrifuged (400×G×10 mins.) to separate the cells and supernatant. The proteinase inhibitors phenyl-methyl sulfonyl-fluoride (2 mM) and tosylamide-2-phenylethylchloromethyl ketone (150 μg/ml) were added to the supernatants. After washing, the cells were lysed in 25 mM Tris-buffered saline pH 7.4 containing 1% Triton X-100 and proteinase inhibitors. Supernatants and cell extracts were stored at −20° C. until use.

Monoclonal Antibodies:

Production of the Monoclonal antibody 7G7/B6. BalbC/J mice (Jackson Labs. Bar Harbor, ME) were injected intraperitoneally and subcutaneously with $20 \times 10^6$ A/Hong Kong influenza virus stimulated PBMC on two occasions 30 days apart, followed by an injection of $14 \times 10^6$ cells intravenously 1 month later. One week after the third injection, immune splenocytes were fused with SP2/0 cells by the method of Ozato, et al, J. Immunol. 124: 533, 1980. Hybridoma culture supernatants, screened by complement mediated lysis which produced antibodies which bound to phytohaemagglutinin (PHA) stimulated lymphoblasts but not B-lymphoblastoid cells from the donor of the influenza-stimulated PBMC, were selected and cloned in microtiter wells on a feeder layer of rat fibroblasts at 0.3 cells/well. One rapidly growing clone which produced large amounts of an IgG2a antibody was selected and designated 7G7/B6. The hybridoma which produces this monoclonal antibody (7G7/B6) has been deposited in the American Type Culture Collection, Rockville, MD. under Accession No. HB8784 A monoclonal anti-HLA-A and -B framework antibody of IgG2a subclass was purchased from Bethesda Research Laboratories, Gaithersburg, MD. Partially purified 7G7/B6 were prepared from ascites by chromatography on Sepharose 4B bound Staphylococcus protein A (Pharmacia Chemicals, Piscataway, NJ), as described by Ey, et al, Immunochem. 15: 429, 1978. Rabbit anti-human IL-2R heteroantibodies are produced following standard procedure using purified IL-2R as an immunogen (Leonard, et al, Nature, 311: 626–631, 1984).

Fluorescence Activated Cell Sorter (FACS) Analysis

Cytofluorometric analysis of the binding pattern of 7G7/B6 to both resting and activated PBMC was done by indirect immunofluorescence utilizing a fluorescein isothiocyanate (FITC) conjugated F(ab')2 fragment of a goat anti-mouse IgG antibody (N. L. Cappell Labs, Cochranville, PA) following routine procedure.

The competitive binding of 7G7/B6 or anti-Tac to activated cells was assessed using biotinylated forms of the monoclonal antibody as described by Titus, et al, J. Immunol. Methods, 50: 193, 1982. PHA activated PBMC were first incubated at 4° C. with unlabelled 7G7/B6 or anti-Tac at a known saturating dose, washed with cold media, and incubated with the biotinylated forms of either the same or alternate monoclonal antibody for 30 minutes at 4° C. The cells were washed with cold media and incubated with 25 μl of a 1/40 dilution of FITC modified Avidin (Sigma) for 30 mins. at 4° C., washed twice and analyzed on the FACS.

The ability of IL-2 to block the binding of antibodies to activated cells was assessed by incubating $1 \times 10^6$ PHA activated PBMC for 1 hr. at 4° C. in a final volume of 100 μl of various concentrations of immunoaffinity purified IL-2 (Robb, et al, Proc. Nat'l. Acad. Sci. USA. 80: 5990, 1983).

Subsaturating doses of biotinylated antibodies were added. The cells were incubated for 30 mins. at 4° C., followed by two washes in cold media, stained with FITC Avidin as above and analyzed on the FACS.

Cell Radiolabelling and Immunoprecipitation Experiments $^{125}$I Cell Surface Labeling:

Tris buffered Saline (TBS) was prepared with 25 mM Tris (BRL) in Dulbecco's PBS (Gibco) at pH 7.4 to which 2 mM phenylmethyl-sulfonyl fluoride, and 150 μg/ml of L-1-tosylamide-2-phenylethylchloro-methyl ketone (Sigma) were added. Lysis buffer consisted of TBS with 1% Triton X-100 (RPI Elk Grove, IL). About one hundred million PHA activated PBMC or HUT 102B2 cells were washed, resuspended in 1 ml. of PBS and surface radiolabeled with 10 μl of $^{125}$I (Na salt, 100 mCi/ml, Amersham, Arlington Hts., IL) by lactoperoxidase (Sigma) catalyzed iodination as described by Ledbetter, et al, J. Exp. Med. 153: 310, 1981. Labeled cells were solubilized at a concentration of $10 \times 10^6$ cells/ml with lysis buffer and the supernatant, after centrifugation, was retained. One ml aliquots of the supernatant were incubated with 2 μg of 7G7/B6, or anti-HLA for 2 hrs. at 4° C. followed by a 1 hr. incubation at 4° C. with washed 10% *Staphylococcus aureus* (Cowan, strain 1, ATCC 12598, Rockville, MD). The suspensions were configured and the immunoprecipitates washed 5 times, and then boiled for 2 mins. in 25 μl of 62.5 mM Tris HCL with 2% sodium dodecyl sulphate (SDS), 10% glycerol, 5% beta-mercaptoethanol, and 0.05% bromophenol blue (all from Sigma). After pelleting the staphylococci, the supernatants were removed and electrophoresed on a 12.5% SDS polyacrylamide gel followed by autoradiographic analysis per standard procedures.

$^{35}$S-Methionine Pulse-Chase Labeling

About hundred million HUT 102B2 cells were washed once in methionine free RPMI 1640 (NIH media unit) containing 2% dialyzed FCS and resuspended at $10 \times 10^6$ cells/ml in the same media for 1 hr. at 37° C. The cells were pelleted, resuspended at $1 \times 10^6$ cells/ml in the same media and pulsed with 250 μCi/ml of $^{35}$S-methionine (1315 Ci/mmol, Amersham) for 30 mins. The cells were pelleted and diluted to $2 \times 10^6$ cells/ml in RPMI 1640 containing excess (500 fold) unlabeled methionine (Gibco). Incubation of the cultures was continued and at intervals of 1, 2, 4, 8, and 22 hours aliquots of $2 \times 10^7$ cells were removed and diluted in a 10 fold volume of 4° C. PBS containing 50 μg/ml of cycloheximide (Sigma). Each aliquot was pelleted and lysed in the same manner as those cells undergoing surface radiolabeling. Prior to immunoprecipitation with 7G7/B6 or anti-Tac, samples were first precleared with anti-HLA. Anti-HLA, 7G7/B6 and anti-Tac immunoprecipitates were analyzed on SDS polyacrylamide gels as above.

Cross Clearing Studies:

Sequential immunoprecipitations were performed on both surfaces as well as biosynthetically labeled HUT 102B2 cells. Aliquots were prepared as described above and immunoprecipitated first with anti-HLA, or 7G7/B6 or anti-Tac. The supernatants from these immunoprecipitates were removed and then immunoprecipitated with either the same or alternate monoclonal antibody (Mab). Optimal doses of the Mab were used in these studies for preabsorption and subsequent immunoprecipitation to ensure the identification of any remaining protein which might be precipitated by the Mab. For the sequential immunoprecipitation studies of the biosynthetically labeled cells, experiments were performed at both an early (<30 mins.) and late (>8 hrs) time point of a pulse chase study.

ASSAY FOR SOLUBLE IL-2 RECEPTOR (IL-2R)

For the ELISA to detect soluble IL-2R, alternate rows of the inner 60 wells of Immulon-1 flat bottomed 96 well microtiter plates (Dynatech) were coated overnight with 150 µl of purified anti-Tac at 1 µg/ml in carbonate buffer pH.9.6 or carbonate buffer alone as a background control. It should be noted here that a heteroantibody, such as a rabbit anti-IL2 receptor antibody, can also be used in place of anti-Tac. In fact, the use of heteroantibody provides a more comprehensive and desirable assay. After washing, 100 µl of various dilutions of samples was added to the coated and control wells, incubated for 2 hrs, washed, and 100 µl of a 1/4,000 dilution of FITC-conjugated 7G7/B6 in phosphate buffered saline containing 1% FCS added to all the wells. After two hour additional incubation, the plates were washed and 100 µl of a 1/1000 dilution of alkaline phosphatase conjugated rabbit anti-FITC was added. After a one hour incubation, the plates were washed, 100 µl of p-nitrophenyl phosphate (Sigma/1 mg/ml) added, and the absorbance of the wells determined after 30 mins. at 450 nM using a Titertek ELISA reader (Flow Laboratories). The ELISA for IgM was performed as described by Yarchoan, et al, J. Immunol. 127, 1958–1964. 1981. The specificity of the ELISA for soluble IL-2R is determined by coating plates with buffer alone, anti-IgM, a monoclonal or polyclonal antibody. These wells then received the day 12 supernatant of PWM activated PBMC, followed by either FITC conjugated anti-IgM (Yarchoan, et al. Immunol. 132, 2696–22699. 1984) or alternatively FITC conjugated 7G7/B6 (Rubin, et al, Hybridoma, 1985), and finally rabbit anti-FITC as described supra.

ALTERNATIVE RADIOISOTOPIC METHOD FOR IL-R

Method:
The wells of a polyvinyl 96 well microtiter plate (Cooke) were coated overnight with 150 ||1 of a solution of the monoclonal antibody 7G7/B≠suspended in carbonate buffer pH 9.6 at 1 µg/ml or 150 ul of carbonate buffer alone. The wells of the plate were washed and 100 µl of various concentrations of detergent solubilized cell extracts or cell-free culture supernatant from the same cells were added to the coated and non-coated (control wells) in triplicate. In this experiment, tonsillar mononuclear cells were activated for 72 hrs. in vitro with phytohemagglutinin. Following a two hour incubation at room temprature, the plates were washed with buffer. (The buffers and diluents employed are the same as those employed for the sandwich ELISA). Each well then received 20,150 cpm of tritium-labelled anti-Tac prepared as described (Leonard, et al, Proc. Nat. Acad. Sci. 80, 6957–6961, 1983) in a volume of 100 ul. After an additional two hour incubation, the plates were washed, dried, and individual wells were cut from the plate The wells were placed in scintillation vials along with 10 ml of scintillation fluid (Ultrafluor) and the radioactivity bound to the wells determined by liquid scintillation-spectroscopy. In all cases the cpm bound to wells coated with carbonate buffer alone was less than 160 cpm.

Molecular Weight Estimation:
Sephadex G-200 gel filtration was performed using the concentrated (10X) supernatant of an IL-2 dependent cell line. Following molecular sieving, the individual fractions (2.5 mls) were lyophilized, resuspended in 100 µl of distilled water and assayed by ELISA to determine IL-2R content. Control and 7G7/B6 immunoaffinity columns were prepared by coupling either normal mouse IgG2a or purified 7G7/B6 to cyanogen bromide activated Sepharose 4B (Pharmacia). Six hundred mls of HUT 102B2 culture supernatant was concentrated and passed first over a normal mouse IgG2a Sepharose 4B column followed by passage over 7G7/B6 Sepharose 4B column. The material bound to the latter column was eluted with a small volume of 0.2M glycine-HCl pH.2.5, dialyzed against PBS, lyophilized, and resuspended in 300 µl of distilled water. 25 ul of this concentrated material was analysed by sodium dodecyl sulfate-polyacrylamide gel electrophoresis (Na-Dod-SO$_4$ PAGE)

ELISA REACTIVITY OF CELL ASSOCIATED AND SUPERNATANT IL-2R

Figure 3:
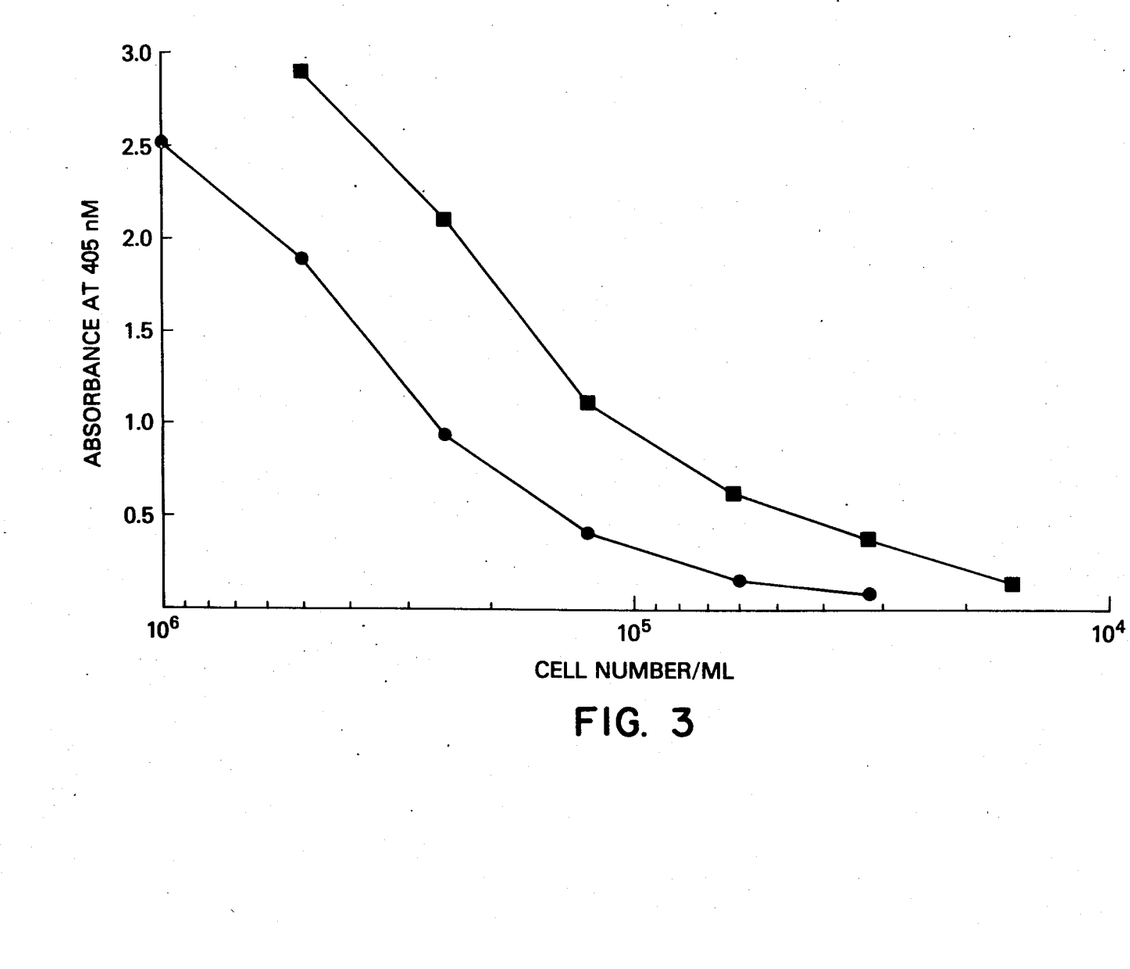
FIG. 3 shows sensitivity of the ELISA for detecting cellular and supernatant IL-2R. An IL-2 dependent T-cell line was stimulated with IL-2 and the culture supernatant (●) and detergent solubilized cells (■) analyzed by ELISA. Absorbance at 405 nM was related to the number of cells from which the cell extract and supernatant were derived.

As shown in FIG. 3 the results indicated that IL-2R was measurable in cell-associated and cell-free supernatants from an IL-2 dependent human T-cell line stimulated with IL-2 at a cell concentration of $1\times10^5$ cells/ml and harvested four days late when the cel concentration was $1\times10^6$ cells/ml. Various dilutions of culture supernatant or detergent extracted cells were analyzed by ELISA and the absorbance at 405 nM plotted against the number of cells from which the supernatant and cell extract were derived. As shown in FIG. 3 both supernatant and cell associated IL-2R could be detected above background levels at cell numbers as low as $6\times10^4$ and $3\times10^4$/ml, respectively. In order to ascertain that the supernatant material was indeed a soluble form of the IL-2R, this supernatant was passed thru a 0.22 micron Millipore filter and also ultracentrifuged for $100,000\times G$ for one hour. Neither procedure diminished the amount of IL-2R detected in the supernatant. To establish the specificity of the ELISA for soluble IL-2R, culture supernatants from PBMC activated for 12 days with PWM were analyzed for IL-2R and IgM. The data in Table 1 show that the absorbance in uncoated wells receiving sample and either FITC anti-IgM or FITC 7G7/B6 (second antibody) plus alkaline phosphatase conjugated anti-FITC (third antibody) was very low. Wells coated with heteroantibody which then received sample and FITC 7G7/B6 (but not FITC anti-IgM), followed by third antibody, were strongly positive. Wells coated with anti-IgM which received sample, FITC anti-IgM (but not FITC 7G7/B6), and third antibody, were also strongly positive. Those wells that were coated with anti-IgM which received sample, FITC 7G7/B6, and third antibody or those wells coated with heteroantibody which received sample, FITC anti-IgM, and third antibody had absorbance comparable to uncoated wells. These results establish that this assay is specific for the molecule bound by 7G7/B6 and heteroantibody.

ACTIVATING STIMULI AND KINETICS OF CELL-ASSOCIATED AND SOLUBLE IL-2R EXPRESSION

Figure 4A:
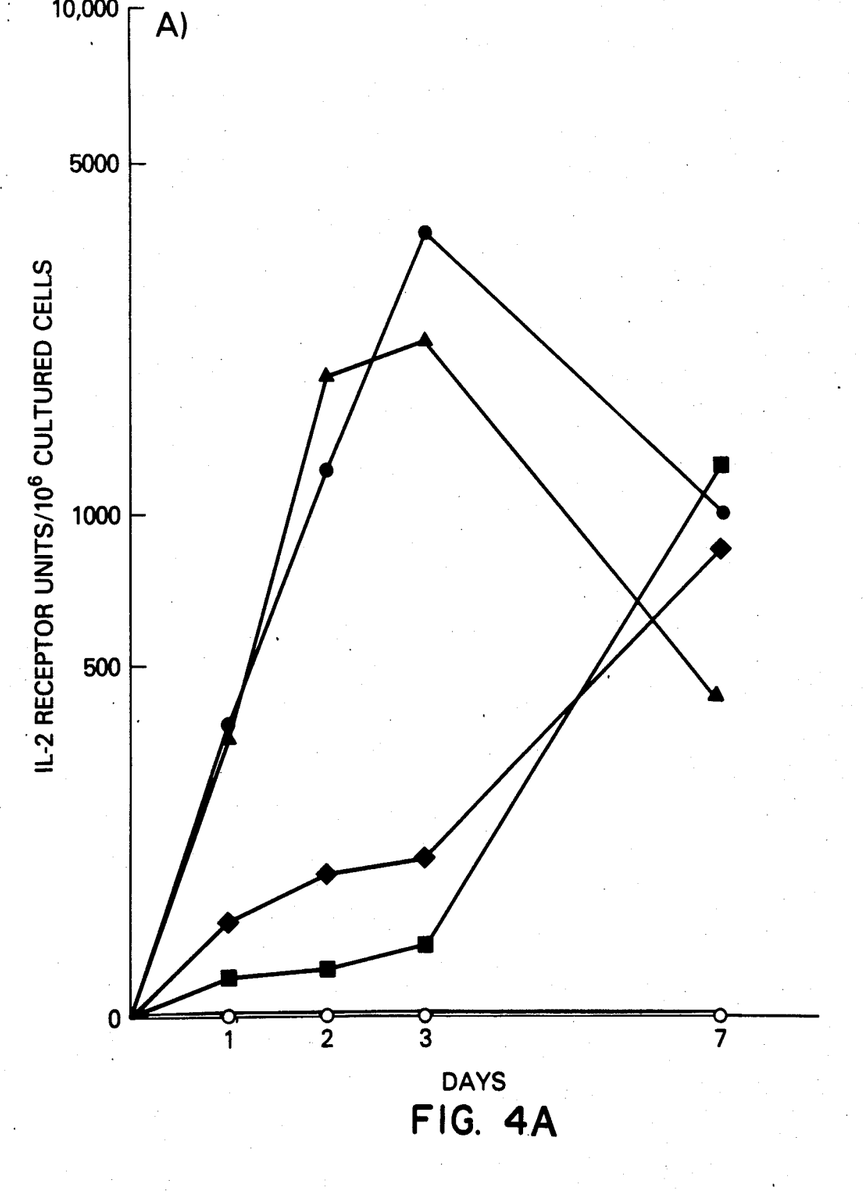
FIG. 4 shows activating stimuli and the kinetics of cellular (A) and supernatant (B) IL-2R generation. Peripheral blood mononuclear cells (PBMC) were cultured in vitro with media (○), PHA (●), OKT3 (▲), tetanus toxoid (■), or allogeneic cells (◆) for various times and the supernatant and cellular IL-2R determined. Results represent the units of IL-2R produced per $10^6$ cultured PBMC.
Figure 4B:
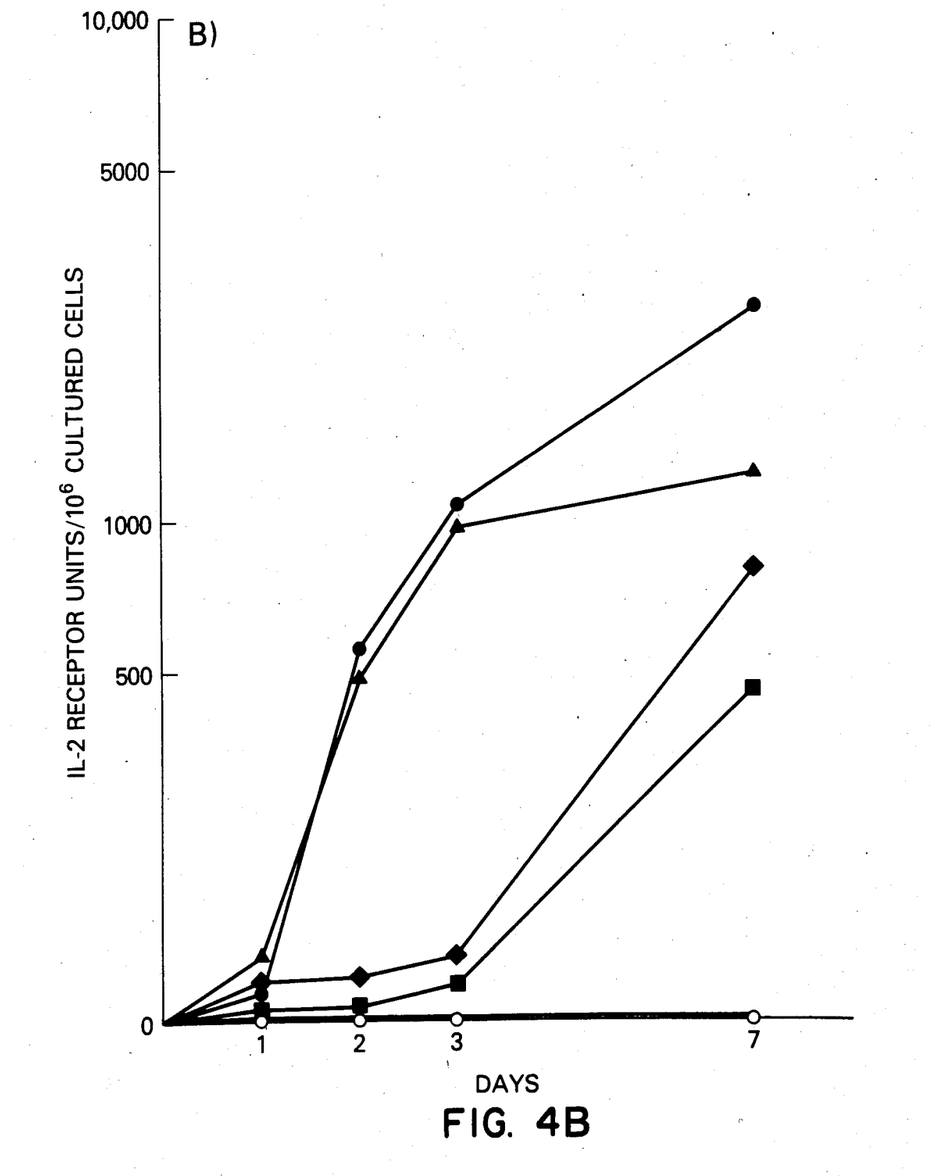

As shown in FIG. 4 A&B, supernatant and cell-associated IL-2R are generated early and with rapid accumulation in those cultures stimulated with PHA or OKT3 while the increase in cultures stimulated with tetanus toxoid and allogeneic cells was more gradual. In addition, cellular and soluble IL-2R generated in response to antigen activation at the time points tested was somewhat less than that produced in response to PHA and OKT3 stimulation.

TABLE 1

| Coating Antibody | Sample | Second Antibody | Third Antibody | Absorbance |
|---|---|---|---|---|
| None | PWM sup. | FITC anti-IgM | Anti-FITC | 0.036 |
| None | " | FITC 7G7/B6 | " | 0.004 |
| anti-Tac | " | FITC 7G7/B6 | " | 2.442 |
| anti-Tac | " | FITC anti-IgM | " | 0.029 |
| anti-IgM | " | FITC anti-IgM | " | 2.346 |
| anti-IgM | " | FITC 7G7/B6 | " | 0.004 |

Legend Table 1
Specificity of an ELISA for Soluble IL-2R. Supernatants were obtained from PWM stimulated PBMC at 12 days of culture. Wells coated with either buffer alone, anti-Tac or anti-IgM received PWM supernatant, followed by either FITC 7G7/B6 or FITC anti-IgMin the combinations shown. All wells then received alkaline phosphatase conjugated anti-FITC. P-nitrophenyl phosphate substrate was added and the absorbance measured at 405 nM.

Cultures stimulated with media alone generated essentially no measurable levels of IL-2R. Cellular IL-2R in cultures stimulated with PHA and OKT3 declined from peak levels on day 7 of culture while supernatant IL-2R continued to rise. To determine if the soluble IL-2R was the result of cell death and subsequent release of cell associated IL-2R, cultures of PBMC stimulated for 24 hrs. with PHA which possessed 500 cell-associated IL-2R Units per $10^6$ cells were washed, either sham treated or repetitively frozen and thawed and placed back in culture in the same supernatant in which they had been generated. The data in Table 2 show that there was no additional accumulation of soluble IL-2R in the supernatant from the killed cells, while the sham treated cells produced soluble IL-2R in the supernatant.

SUPERNATANT IL-2R GENERATION IS RADIORESISTANT BUT REQUIRES PROTEIN SYNTHESIS

Figure 5A:
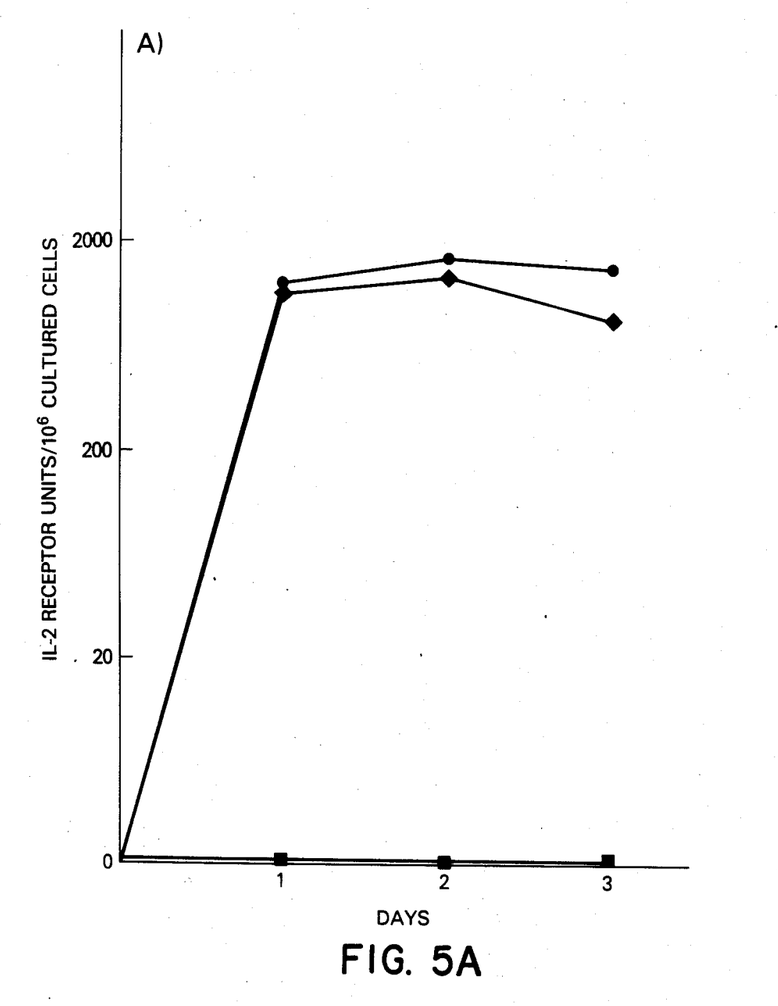
FIG. 5 shows that soluble IL-2R production requires de novo protein synthesis but not cellular proliferation. Peripheral blood mononuclear cells were stimulated with PHA with no treatment (●), following irradiation with 3000 R (◆) or in the presence of 25 μg/ml cycloheximide (■). Both cellular (A) and supernatant (B) IL-2R were determined. Results represent the units of IL-2R produced per $10^6$ cultured PBMC.
Figure 5B:
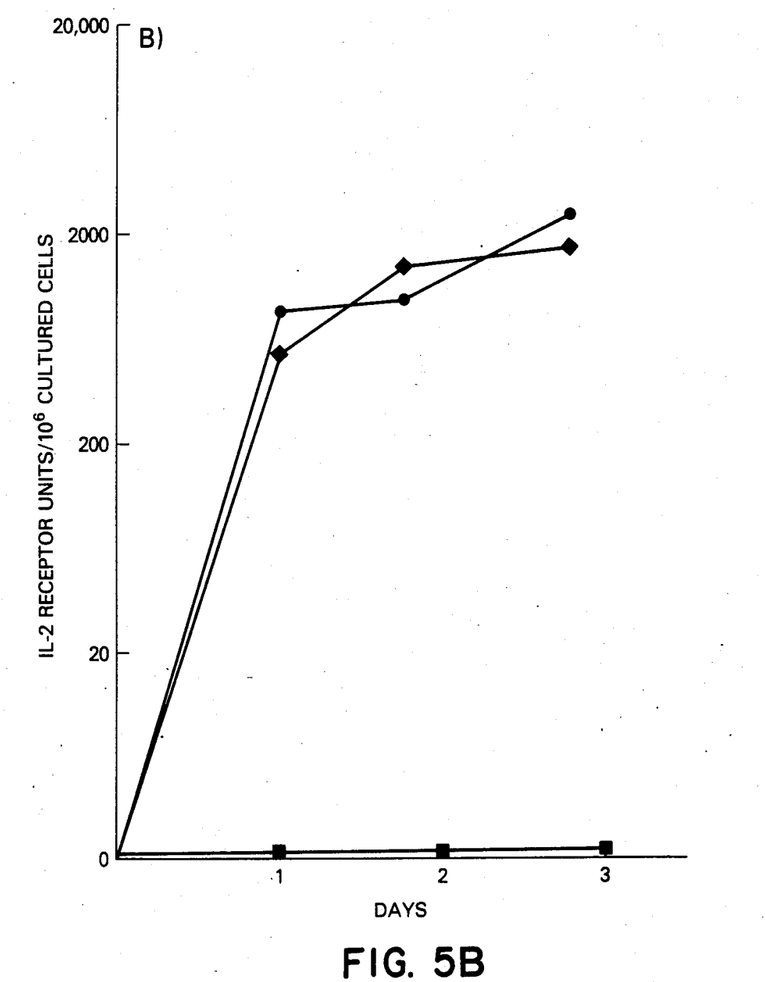

Since cell-associated IL-2R expression has been shown to require de novo protein synthesis but not celular proliferation, (Uchiyama, et al, supra) the effect of irradiation and of polypeptide synthesis inhibitor cycloheximide on supernatant IL-2R was examined FIGS. 5, A&B show that irradiation with 3000R did not inhibit supernatant or cell-associated IL-2R generation while cycloheximide (25 μg/ml) completely inhibited the generation of both forms of IL-2R.

TABLE 2

| | Supernatant IL-2R Levels on Day | | |
|---|---|---|---|
| Treatment | 1 | 2 | 3 |
| None | 187 | 674 | 1265 |

TABLE 2-continued

| | Supernatant IL-2R Levels on Day | | |
|---|---|---|---|
| Treatment | 1 | 2 | 3 |
| Freeze/Thaw | 187 | 195 | 158 |

Legend Table 2
Soluble IL-2R is not released from killed IL-2R positive cells in vitro. Normal PBMC were activated with PHA for 24 hours and the quantity or soluble and cellular IL-2R determined by ELISA. These activated cells were then subjected to three cycles offreezing and thawing or sham treated and returned to the same IL-2 and IL-2R containing media for additional periods of in vitro culture. The level of supernatant IL-2R was determined by ELISA. Results represent the Units of IL-2R per $10^6$ cultured PBMC.

ANALYSIS OF CELL LINES FOR THE CAPACITY TO RELEASE IL-2R

Because HTLV I infected T-cell lines constitutively express cell surface IL-2R (Robb, et al, J. Exp. Med. 160, 1126–1146, 1984), the cells and supernatants of several human tumor cell lines were examined for IL-2R. The data in Table 3 show that the HTLV I positive T-cell line HUT 102B2 expressed high levels of cell associated IL-2R, and also released large amounts of IL-2R into supernatants compared to the levels of IL-2R expressed and released by an IL-2 dependent cell line. HTLV I negative T-cell lines such as MOLT 4, JURKAT, and CEM did not express cellular IL-2R nor release soluble IL-2R. The pre B-cell lines NALM-1 and NALL-1, and the B-cell lines NU-DHL1 and SU-DHL6, did not express or release IL-2 R into culture supernatants. In contrast, all three EBV induced B-cell lines expressed low levels of cellular IL-2R and one of these lines released measurable IL-2R into the culture supernatant.

MOLECULAR WEIGHT ESTIMATION OF THE RELEASED SOLUBLE IL-2R

Figure 6:
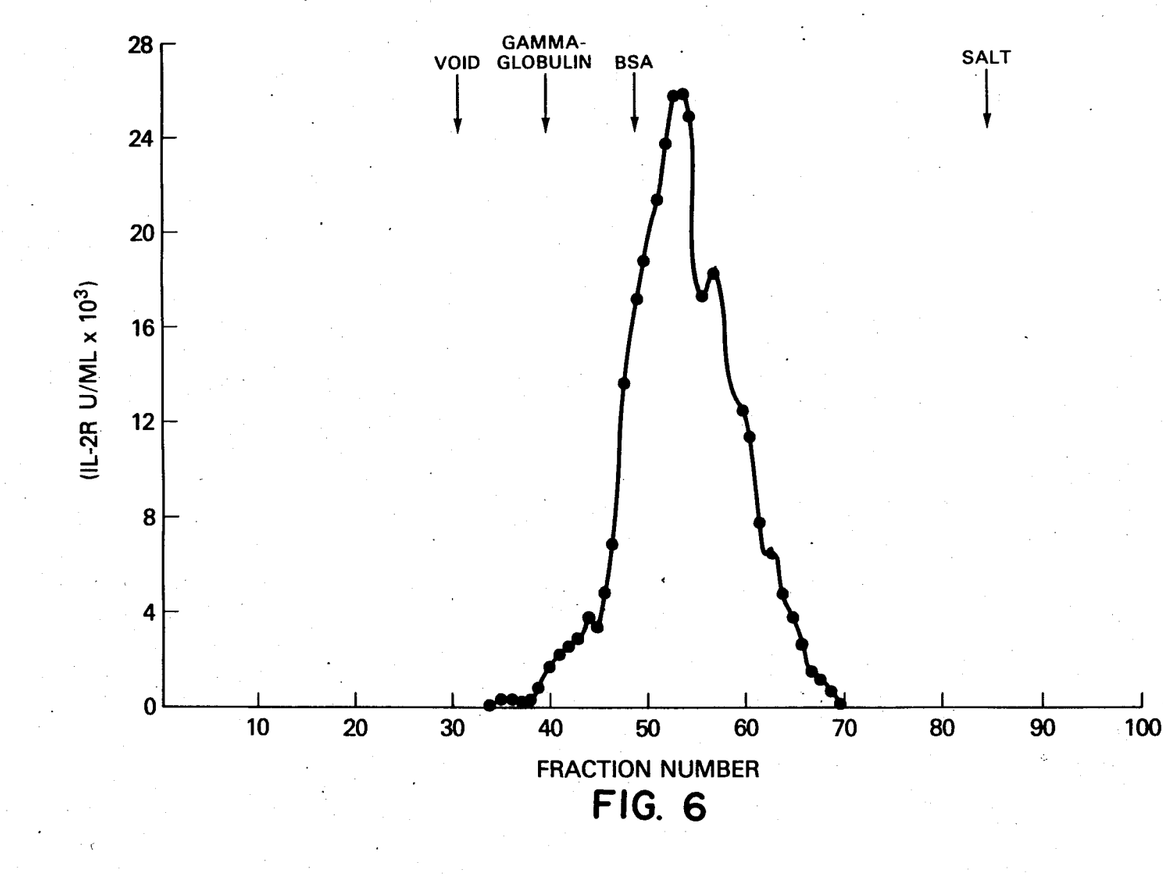
FIG. 6 shows molecular weight estimation of soluble IL-2R by Sephadex G-200 gel filtration. Concentrated supernatant from an IL-2 dependent T-cell line was sieved on a calibrated Sephadex G-200 column and the amount of IL-2R in the fractions determined by ELISA.
Figure 7:
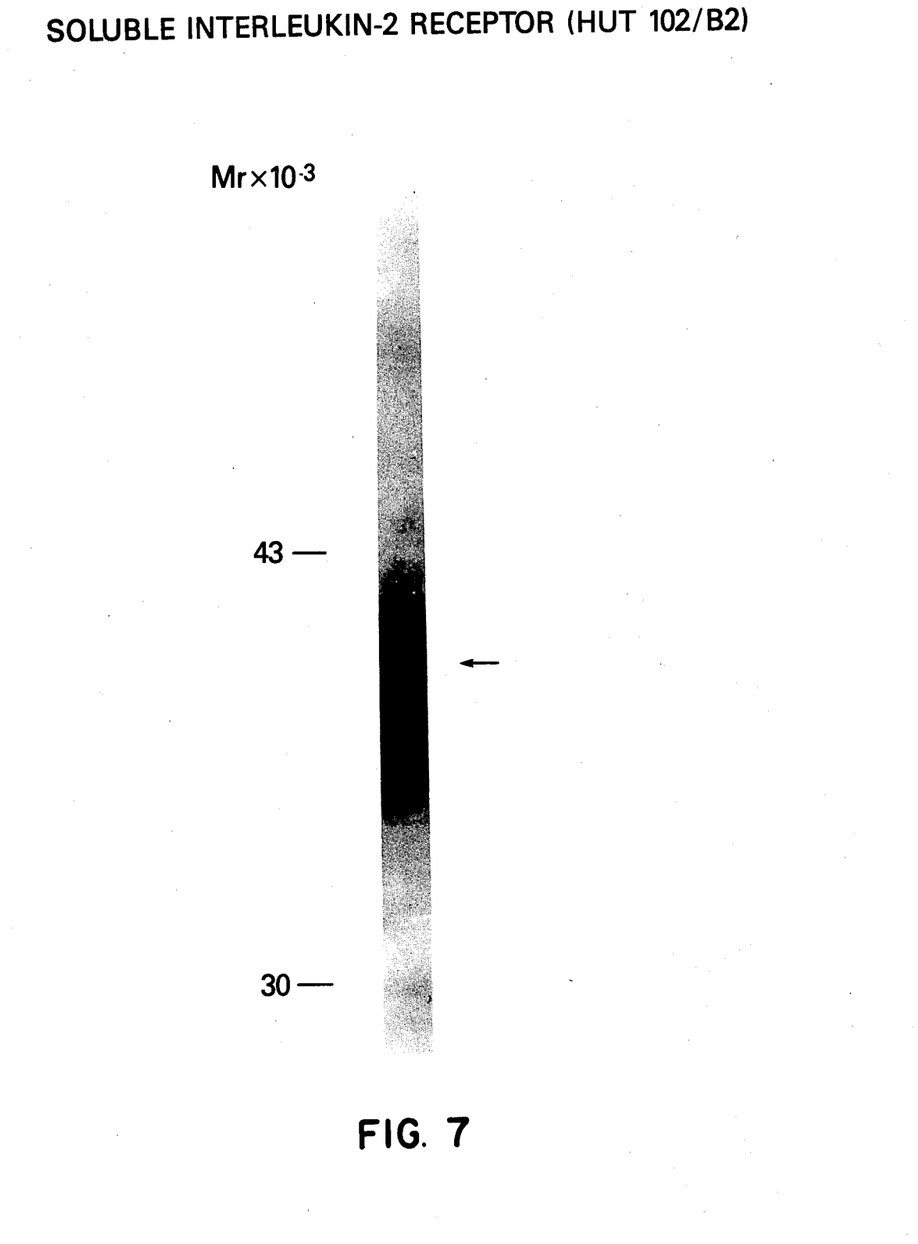
FIG. 7 shows molecular weight estimation of soluble IL-2R by NaDodSO$_4$-PAGE. Supernatant IL-2R from HUT 102B2 was first passed over a normal mouse IgG2a Sepharose 4B column and then over a monoclonal anti-IL-2R (7G7/B6) Sepharose 4B column. The 7G7/B6 column was extensively washed with phosphate buffered saline and then eluted with 10 ml of 0.2M glycine HCl. The eluted protein was lyophilized, resuspended in 300 μl of distilled water, and 25 μl analyzed on a 12.5% NaDodSO$_4$ polyacrylamide gel under reducing conditions, followed by silver staining. (Molecular weight markers: ovalbumin—43,000; carbonic anhydrase—30,000).

The soluble IL-2R from an IL-2 dependent T-cell line analyzed by Sephadex G-200 gel filtration (FIG. 6) appears to be relatively uniform in size with a molecular weight somewhat smaller than albumin. To better define the molecular weight of the soluble IL-2R, immunoaffinity purified soluble IL-2R from HUT 102B2 cells was analyzed by NaDodSO4 PAGE. FIG. 7 shows that the soluble IL-2R migrated as a single broad band of apparent molecular weight Mr=40,000.

TABLE 3

| Cell Line | Cell Type | Cellular IL-2R | Supernatant IL-2R |
|---|---|---|---|
| IL-2 dependent line | T-cell | 1,250 | 1,000 |
| HUT-102B2 | T-cell | 4,800 | 11,000 |
| CEM | T-cell | <31.3 | <31.3 |
| JURKAT | T-cell | <31.3 | <31.3 |
| MOLT-4 | T-cell | <31.3 | <31.3 |
| NALM-1 | pre-B-cell | <31.3 | <31.3 |
| NALL-1 | pre-B-cell | <31.3 | <31.3 |
| EBV-1 | B-cell | 54.3 | <31.3 |
| EBV-2 | B-cell | 55.0 | <31.3 |
| EBV-3 | B-cell | 205.0 | 65.0 |
| NU-DHL1 | B-cell | <31.3 | <31.3 |
| BU-DHL6 | B-cell | <31.3 | <31.3 |

Legend Table 3
Analysis of Various Cell Lines for the Presence of cellular and Supernatant IL-2R. In vitro cultured cell lines were analyzed for the level of cellular and supernatant IL-2R receptors by ELISA. Results represent the Units of IL-2R per $10^6$ cultured cells.

The "Sandwich" ELISA

The term "sandwich" ELISA or "sandwich" assay as used herein means that at least two antibodies or reactive fragments thereof having different binding sites on IL-2R are used as if the receptor were sandwiched between these two antibodies. These antibodies could either be both monoclonal or one monoclonal and the other a heteroantibody (polyclonal) or both could be heteroantibody.

Figure 1:
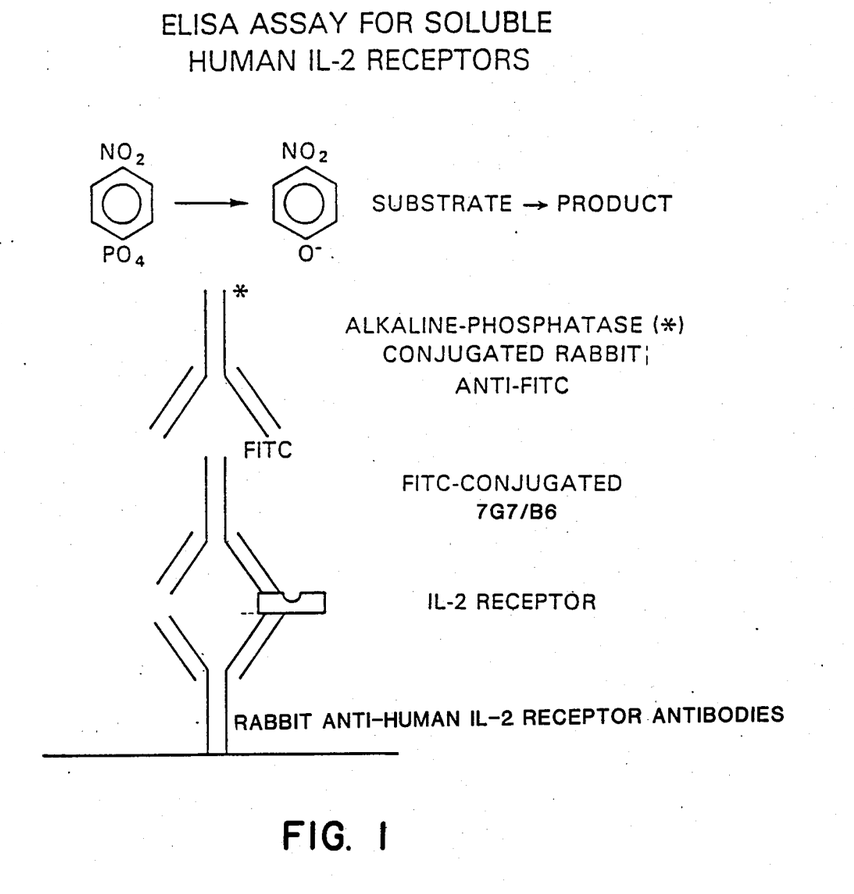
FIG. 1 schematically shows various steps of the ELISA for soluble human IL-2R.

As shown in FIG. 1, rabbit anti-human IL-2 receptor antibody is diluted to a desired concentration (1 to 1200) in carbonate buffer pH 9.6 and 150 μl added to the wells of alternate columns of the inner 60 wells of Immulon-1 flat-bottomed 96-well microtiter plates (Dynatech). The alternate wells of the plate receive carbonate buffer alone. Following overnight or longer incubation at 4° C., the wells are washed with buffer (phosphate buffered saline pH 7.4 containing 0.05% tween and sodium azide), and various dilutions of the sample to be analyzed are applied to the coated and non-coated wells. The diluent consists of phosphate-buffered saline containing tween, azide, and 1% fetal calf serum or other protein source (diluent). A reference preparation of soluble IL-2 receptors is also added to the coated and non-coated wells. Following a two hour incubation at room temperature, the plates are washed with buffer (PBS with tween and azide as above) and 100 μl of a 1:1000 dilution of fluorescein isothiocyanate (FITC)-conjugated monoclonal antibody (7G7/B6) is added and the plates incubated for 2 hrs. at room temperature. Following this incubation, the plates are washed and 100 μl of alkaline phosphatase conjugated rabbit anti-FITC diluted 1:1000 in diluent is added. After a 1 hr. incubation, the plates are washed and 100 μl of a solution of p-nitro phenylphosphate (PNPP, Sigma, 1 mg/ml) substrate in diethanolamine buffer pH 9.8 added to the wells. The conversion of substrate (PNPP) to product (PNP) is determined by absorbance at 405 nM in the experimental (coated) and control (uncoated) wells and the latter subtracted from the experimental wells. The specific product produced in the experimental wells is then related to that produced in the standard wells and the amount of IL-2R present in an unknown sample is determined from the readings obtained for various known levels of IL-2R.

It should be noted that the preferred embodiment of the method described, supra, is an indirect or "amplified" Enzyme-Linked Immunosorbent Assay (ELISA). Of course, multiple modifications of the present method can be devised by the artisan in accordance with the description outlined herein. Some alternatives to the method include: (A) The soluble molecules (IL-2R) are measurable either using solid phase assays, fluid phase assays, or semi-solid phase assays (antibody or ligand in gel). The method need not be limited to only solid-phase systems as should be evident to one of ordinary skill in the art to which this invention pertains.

(B) In the case of solid phase assays, the soluble IL-2 receptor can be captured for analysis by materials binding either non-specifically or specifically to the receptor. To ensure specificity of the assay, however, the former must detect receptor by a specific means, e.g. antibody, IL-2, or other specific ligand. Such antibodies include, but are not limited to, heteroantisera (all various species) binding to the receptor, monoclonal heterologous and homologous antibodies (hybridoma derived or otherwise), and by specific ligand (IL-2). In those cases where the receptor is captured using materials which are specific to the receptor including heterologous and homologous antisera, monoclonal antibodies (hybridoma derived or otherwise), and specific ligand (IL-2) binding to the receptor, a non-specific means of detecting the receptor can be employed such as heteroantisera containing antibodies to the human IL-2R as well as certain ligands binding to various epitopes on the molecule which are not-specific to the molecule, e.g. sugar residues and the like.

(C) If captured on a solid surface for analysis, the solid surface may consist of polymeric compounds, glass or ceramic materials, inorganic matrices, agarose, magnetic beads, and other adsorbents well known in the art.

(D) The specific or non-specific materials binding to the receptor could be "tagged" with various enzymes (alkaline-phosphatase, glucose oxidase, peroxidase, and the like); radioisotopes ($I^{125}$, $H^3$, $C^{14}$ and the like) or other materials to allow the detection of binding. In addition, "competitive" assays could be established in which the binding of labeled ligand to the receptor is inhibited by the binding of "cold" or non-labeled ligand. It should be noted that in addition to the "indirect or amplified" assays, ligand binding directly to the receptor could also be used for the detection of receptor. Furthermore, a plurality of layers of reagents could be used to "amplify" the assay.

(E) It should be emphasized that the buffers, the incubation times, the substrate, the enzyme and the like mentioned here are only exemplary. Of course, any of the described incubation times the buffers employed for binding the antisera or ligand to the solid surface, the buffers used for washing, diluting, or substrate solubilization, and the wavelength of light used for determining the conversion of substrate to product could be suitably modified. Any suitable substrate which will produce a product measurable at a wavelength different from that of the substrate can-also be employed.

(F) Another method to detect the receptor would be to allow binding of the specific ligand to the receptor then detect the presence of the ligand by antibodies to the ligand either by an indirect or direct method.

(G) If analyzed in the fluid phase any suitable solvent can be employed. In the fluid phase, the assay could be performed as a standard competitive radioimmunoassay involving radiolabeled IL-2 receptor, antibody to the IL-2 receptor (7G7/B6 or other antibodies), a ligand binding to the anti-receptor antibody but not to the IL-2 receptor and non-radiolabeled IL-2 receptor. In addition to the use of radioisotopically labeled IL-2R, the receptor could be labeled with enzyme or other materials to allow its detection. Other fluid phase assays could involve "tagged" IL-2 to detect the receptor in the fluid phase as well as salt or other methods to precipitate the receptor ligand complex.

(H) In addition to absorbance changes noted during the enzymatic conversiton of substrate to produce, this assay can also be conducted using radioisotopic means, for example as shown in Table 4. As can be seen, soluble IL-2 receptors can be measured by the binding of $^3H$-labeled monoclonal antibodies. The data also show that IL-2 can be detected either in cell extracts or culture supernatants. In addition, the conversion of radioisotopic substrate to non-radioisotopic product can also be used. However, the non-radioactive, ELISA as described supra is the preferred method.

TABLE 4

Table 4. A solid phase radioisotopic method for the measurement of soluble IL-2 receptors.

| Source of Soluble IL-2R | Units of IL-2R/ml# | CPM of Tritiated anti-IL-2R Bound |
|---|---|---|
| Detergent solubilized cells | 24,800 | 6,956 ×/÷ 1.07* |
| " | 12,400 | 7,886 ×/÷ 1.01 |
| " | 6,200 | 7,887 ×/÷ 1.01 |
| " | 3,100 | 5,459 ×/÷ 1.01 |
| " | 1,550 | 2,967 ×/÷ 1.01 |
| Culture supernatant | 4,600 | 5,059 ×/÷ 1.02 |
| " | 2,300 | 3,038 ×/÷ 1.03 |
| " | 1,150 | 1,706 ×/÷ 1.03 |
| " | 575 | 940 ×/÷ 1.07 |
| " | 288 | 597 ×/÷ 1.01 |
| " | 144 | 351 ×/÷ 1.04 |

*Values represent the geometric mean Counts Per Minute ×/÷ 1 Standard Error of the Mean of Tritiated anti-Tac bound to the plates.
The concentration of soluble IL-2R in these preparations in Units/ml was determined by the sandwich ELISA.

The demonstration herein that the release or expression of IL-2R is associated with immune activation makes it now possible to monitor the cell-associated and soluble IL-2R in various body fluids as a sensitive test of altered states of immune activation, such as occurs in rheumatoid arthritis and systemic lupus erythematosis, for example. The ELISA test of the present invention can, be valuble to predict when disease exacerbations are about to occur and/or in monitoring immunosuppressive therapy. In a similar way determination of IL-2R in the serum of individuals rejecting allografted kidneys, livers and the like would allow monitoring graft rejection and titrating immunosuppressive therapy.

Figure 2:
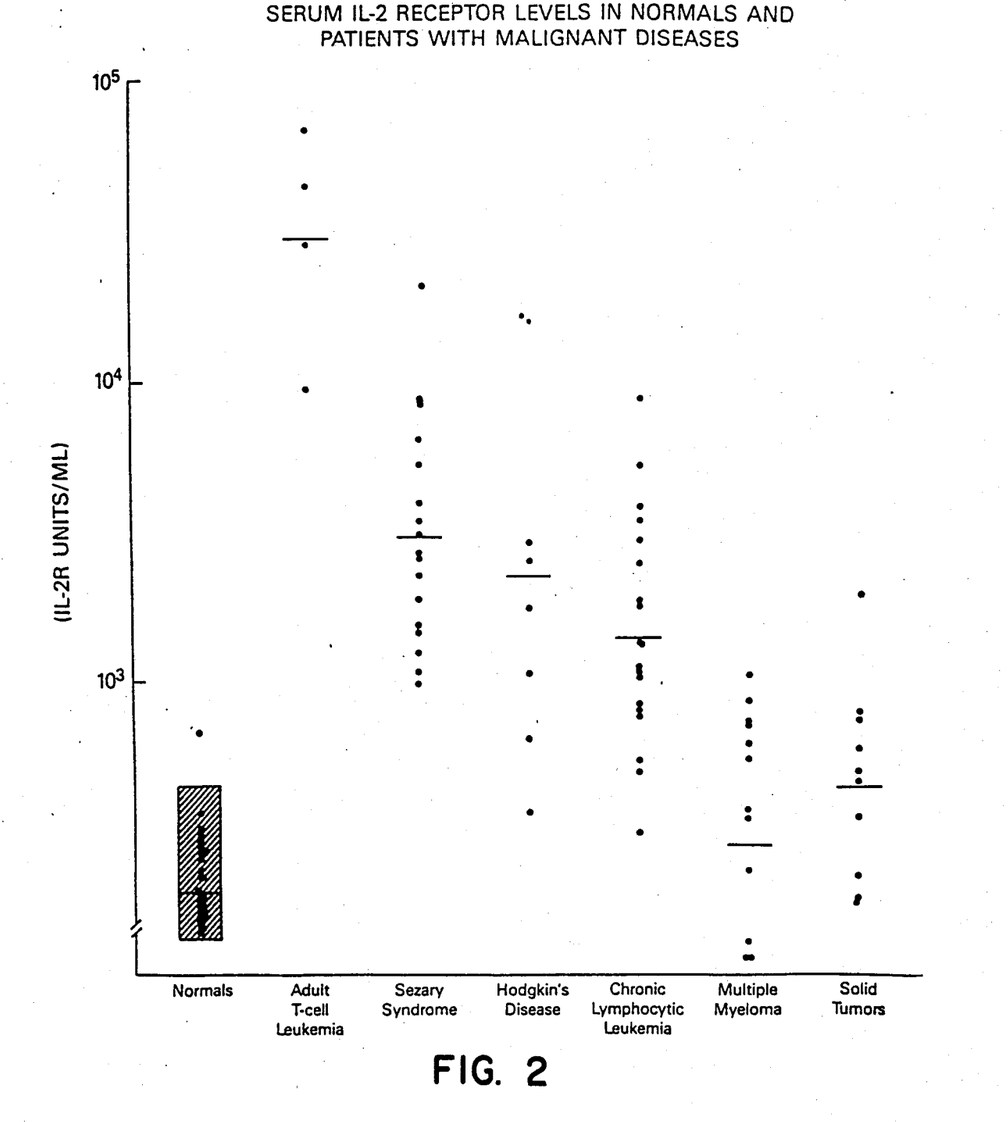
FIG. 2 shows serum IL-2R levels in normals and patients with several malignant diseases.

The demonstration of elevated serum levels of IL-2R in association with certain malignancies as shown in FIG. 2, establishes that an analysis of cells and serum from certain patients with such cancers is a useful diagnostic means for detecting and/or monitoring initial or residual tumor burden.

It should be noted that the present sensitive assay for IL-2R also enables the dosage of IL-2R administered to humans to be monitored much as the serum levels of pharmaceuticals are checked.

Since the present test for soluble IL-2R requires hybridoma derived monoclonal antibodies which can be produced in large quantities, the quantities of reagents needed is no longer a problem. Mice (costing approximately $10 each) injected with the hybridoma cells, would generate enough reagents for the performance of roughly 50,000 tests making it obviously quite inexpensive. The performance of this test as an Enzyme-Linked Immunosorbent Assay (ELISA) requires no radioisotopes and the reagents are stable over a period of about one year, which are significant advantages of the present invention.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for quantitative determination of soluble interleukin-2 receptor (IL-2R) leveL in a cell free sample comprising the steps of:
   (a) coating suitable number of wells in a multiwell microtiter plate with immunoglobulin containing antibody against soluble IL-2R;
   (b) washing the wells with a suitable medium to remove excess unbound antibody;
   (c) adding a sample of human body fluid suspected of containing soluble IL-2R to the wells and incubating for sufficient time for binding between antibody and said sample to occur;
   (d) washing the wells with suitable medium to remove unbound sample;
   (e) adding to the wells sufficient amount of fluoresceinisothiocyanate (FITC) modified monoclonal antibody against IL-2R, said monoclonal antibody being different from that in step (a) if the antibody in step (a) is also a monoclonal antibody, incubating for sufficient time for binding between the monoclonal antibody and said sample to occur;
   (f) washing the wells with suitable medium to remove unbound FITC modified antibody;
   (g) adding to the wells enzyme-conjugated anti-FITC antibody and incubating for sufficient time for binding to occur;
   (b) washing the wells with suitable medium to remove unreacted anti-FITC antibody and;
   (i) adding sufficient amount of suitable substrate for said conjugated enzyme and measuring for resulting product relative to known amounts of IL-2R similarly treated as in steps (a) thru (i) and then determining the level of binding between the soluble receptor and the FITC modified monoclonal antibody by comparing with a control sample or a standard curve.

2. A method for detecting the presence of soluble interleukin-2 receptor in a cell free sample comprising reacting a cell free sample of human body fluid in which the presence of soluble interleukin-2 receptor is to be determined with a plurality of ligands, each ligand having binding affinity for a specific site on the soluble interleukin-2 receptor, said site being different for each ligand, and then determining the occurence of binding between said ligands and the receptor by comparing with control sample or a standard curve.

3. The method of claim 2 employing at least two ligands different from each other.

4. The method of claim 3 wherein at least one of the ligands is a monoclonal antibody or a fragment thereof.

5. The method of claim 4 wherein said monoclonal antibody is obtained from a hybridoma having American Type Culture Collection, Accession No. HB8784.

6. The method of claim 3 wherein at least two ligands are monoclonal antibodies or fragments thereof.

7. The method of claim 3 wherein at least two ligands are heteroantibody or fragments thereof.

8. The method of claim 4 wherein only a second ligand is a heteroantibody or fragment thereof.

9. The method of claim 3 wherein one of the ligands is interleukin-2 or a fragment thereof.

10. The method of claim 9 wherein a second ligand is an antibody.

11. The method of claim 2 determining said binding enzymatically, radioisotopically, spectrophotometrically, immunologically, fluorescentphotometrically or a combination thereof.

12. The method of claim 2 determining said binding by a competitive immunoassay employing radiolabeled and unlabeled ligands.

13. A monoclonal antibody obtained from a hybridoma having American Type Culture Collection, Accession No. HB8784.

14. A method of detecting immune activation in humans comprising detecting the presence of soluble interleukin-2 receptor in body fluid by the method of claim 2.

15. The method of claim 14 wherein said immune activation is that of the lymphoreticular system.

16. A method of detecting malignancy which produces soluble interleukin-2 receptor (IL-2R) comprising detecting the presence of soluble IL-2R in body fluid by the method of claim 2.

17. The method of claim 16 wherein said malignancy is that of the lymphoreticular system.

18. A kit for assaying soluble interleukin-2 receptor (IL-2R) in human body fluid comprising a first container containing sufficient amount of a ligand which binds to soluble IL-2R found in human body fluid; a second container having a different ligand binding to a different site of said soluble IL-2R, said different ligand being detectable by a method selected from the group consisting of enzymatic, radioisotopic, spectrophotometric, immunologic, fluorescentphotometric and combination thereof.

* * * * *